(12) United States Patent
Mukai et al.

(10) Patent No.: US 7,959,807 B2
(45) Date of Patent: Jun. 14, 2011

(54) METHOD FOR RECOVERING USEFUL COMPONENTS FROM DYED POLYESTER FIBER

(75) Inventors: Kouji Mukai, Matsuyama (JP); Minoru Nakashima, Matsuyama (JP)

(73) Assignee: Teijin Fibers Limited, Osaka (JP)

( * ) Notice: Subject to any disclaimer, the term of this patent is extended or adjusted under 35 U.S.C. 154(b) by 549 days.

(21) Appl. No.: 11/996,229

(22) PCT Filed: Jul. 31, 2006

(86) PCT No.: PCT/JP2006/315541
§ 371 (c)(1),
(2), (4) Date: Jan. 18, 2008

(87) PCT Pub. No.: WO2007/018161
PCT Pub. Date: Feb. 15, 2007

(65) Prior Publication Data
US 2009/0133200 A1      May 28, 2009

(30) Foreign Application Priority Data

Aug. 5, 2005   (JP) ................................ 2005-227768

(51) Int. Cl.
B01D 11/02   (2006.01)

(52) U.S. Cl. ....... 210/634; 210/774; 210/806; 264/37.1; 521/48; 521/48.5; 528/272; 528/491; 528/502 R; 528/502 A; 528/503; 203/39

(58) Field of Classification Search .............. 8/102, 440; 203/28.29, 39, 47; 210/634, 638, 639, 749, 210/774, 805, 806; 264/36.1, 37.1; 521/48, 521/48.5; 560/76, 78, 96, 98; 528/272, 274, 528/480, 491, 502 R, 502 A, 503
See application file for complete search history.

(56) References Cited

U.S. PATENT DOCUMENTS

| | | | | | |
|---|---|---|---|---|---|
| 1,839,819 | A | * | 1/1932 | Whitehead ........................ 8/440 |
| 3,108,082 | A | * | 10/1963 | Riehl et al. ....................... 521/48 |
| 4,064,079 | A | * | 12/1977 | Sidebotham et al. ............ 521/48 |
| 4,165,217 | A | * | 8/1979 | Kitamura et al. .................. 8/440 |
| 5,236,959 | A | * | 8/1993 | Oakley et al. ................. 521/48.5 |
| 5,668,186 | A | * | 9/1997 | Brunelle et al. ................. 521/48 |
| 5,952,520 | A |  | 9/1999 | Naujokas |
| 5,989,296 | A | * | 11/1999 | Patton et al. ....................... 8/440 |
| 2005/0027023 | A1 | * | 2/2005 | Masuda et al. ................... 521/48 |
| 2006/0074136 | A1 | * | 4/2006 | Smith et al. ...................... 521/48 |

FOREIGN PATENT DOCUMENTS

| | | |
|---|---|---|
| JP | 48-061447 A | 12/1971 |
| JP | 11-021374 A | 1/1999 |
| JP | 2000-169623 | 6/2000 |
| JP | 2003-128626 A | 5/2003 |
| JP | 2004-217871 A | 8/2004 |
| JP | 2004-300115 A | 10/2004 |

* cited by examiner

Primary Examiner — Joseph W Drodge
(74) Attorney, Agent, or Firm — Sughrue Mion, PLLC

(57) ABSTRACT

To establish an efficient and economical useful component recovery method capable of recovering high purity useful components from a dyed polyester fiber.

A method for recovering useful components from a dyed polyester fiber, includes a dye extraction step, a solid liquid separation step, a depolymerization reaction step, an ester interchange reaction step, and a useful component separation step, for recovering useful components from the dyed polyester fiber, wherein the dye extraction step includes a step of extracting and removing a dye at the glass transition temperature of the polyester or higher and at 220° C. or less with a xylene extracting solvent and an alkylene glycol extracting solvent in combination.

12 Claims, No Drawings

METHOD FOR RECOVERING USEFUL COMPONENTS FROM DYED POLYESTER FIBER

TECHNICAL FIELD

The present invention relates to a method for recovering useful components in polyester production from a polyester fiber containing a dye.

BACKGROUND ART

Polyester such as polyethylene terephthalate has been widely used as a fiber, a film, a resin, or the like because of its excellent characteristics. Effective utilization of polyester remnants in the form of a fiber, a film, or the like, produced in the production process thereof is not only important for reducing the cost of the products but also a large problem regarding the environment. As the disposal methods therefor, various proposals by material recycle, thermal recycle, and chemical recycle have been made. Out of these, with the material recycle, for polyester resin remnants of PET bottles, and the like, PET bottles are recovered, and positive reuse thereof are carried out by municipalities acting as the centers. However, to fiber remnants, this recycle method has been very difficult to apply.

Whereas, the thermal recycle for converting polyester wastes into fuel has a feature of reuse of the heat of combustion of polyester wastes. However, the heat value per unit weight of polyester is relatively low. Therefore, large heat generation cannot be effected unless a large quantity of polyester wastes are burned. Accordingly, there is a problem that the polyester raw material is not effectively utilized, which is not preferable from the viewpoint of the conservation of natural resources. In contrast, with the chemical recycle, polyester wastes are recycled into polyester raw materials. For this reason, the degradation of quality caused by recycling less occurs, and the recycle is excellent as recycle of a closed loop. This closed loop represents a loop going through one cycle of from polyester raw materials, polyester fiber products, consumption by users, recovery of used polyester products, and recycle factories of polyester products, and back to polyester materials.

With the chemical recycle, the recycling is mostly targeted for resin remnants and film remnants. As the methods for recycling polyester fiber remnants, for example, considering based on polyethylene terephthalate which is typical polyester, JP-A-48-61447 discloses the following method, and other methods: polyester remnants are depolymerized with an excess of ethylene glycol (which may be hereinafter abbreviated as EG), and then, the resulting bis-β-hydroxy ethylene terephthalate is directly polycondensed to obtain regenerated polyester. However, with this method, in the depolymerization reaction step, polyester remnants and EG are charged both together in a depolymerization reaction tank for depolymerization. Therefore, in some cases, the charged polyester remnants may form agglomerates inside the reaction tank, which makes stirring impossible. For this reason, unfavorably, the inside of the depolymerization reaction tank becomes ununiform, and the depolymerization time becomes longer. Further, with this method, the amount of EG to be used for depolymerization is large. This unfavorably results in not only economical disadvantages, but also the formation of impurities such as diethylene glycol in depolymerization. This also results in the following defects: the physical properties of the resulting polyethylene terephthalate, particularly, the softening point thereof is remarkably deteriorated, and only polyethylene terephthalate (which may be hereinafter abbreviated as PET) low in physical properties can be obtained. Thus, in the related art, the technology for efficiently disposing of polyester fiber remnants has not been completed yet.

Polyester, for example, polyalkylene terephthalate, particularly, PET is produced in large amounts for use in fibers, films, beverage bottles, other resin formed products, or the like because of its excellent chemical stability.

However, the disposal of wastes of fibers, films, bottles, or other resin products, or PET of nonstandard products generated in large amounts with the increase in production and usage is currently becoming a large social issue. Under such circumstances, regarding the material recycle, the chemical recycle, the thermal recycle, or the like, various proposals have been made on the recycling methods.

On the other hand, out of the wastes, particularly, disposal of PET bottles is becoming even more serious due to the bulkiness. However, as the recycling method, only recycling of such a degree as to melt the recovered used PET bottles again into fiber is carried out as the material recycle. When merely the recovered used PET bottles are melt molded to manufacture bottles, it is impossible to use the bottles as PET bottles again due to the reduction of the physical properties.

Whereas, for the reuse method in which PET bottles are washed, and filled again, the method cannot be a permanent measure from the viewpoints of the payer of recycling cost, the safety, and the hygiene, and because of the facts that there is a limit on the number of reuses, and that the bottles end up by being disposed of, and other facts. Further, PET bottle remnants may include therein different types of plastics such as polystyrene (which may be hereinafter abbreviated as PS), polypropylene (which may be hereinafter abbreviated as PP), polyethylene (which may be hereinafter abbreviated as PE), polyvinyl chloride (which may be hereinafter abbreviated as PVC), or other polyolefin resins derived from components of PET bottles such as labels, shrink films, base cups, or caps, aluminum derived from aluminum cans, iron derived from steel cans, adhesives, pigments, dyes, or the like.

Also to separately recovered PET bottle bales (compressed and baled PET bottles), mixing of foreign matter materials is difficult to avoid. Also, in the chemical recycle in which decomposition into monomers forming PET is carried out by the use of water or a solvent such as methanol (which may be hereinafter abbreviated as MeOH) or EG for reuse, in the process of the heating operation or the reaction operation, foreign matter materials may generate various decomposed gases (e.g., hydrogen chloride gas) and various decomposed products (e.g., lower hydrocarbon), or the mixed matters themselves may remarkably reduce the purity of the recovered dimethyl terephthalate (which may be hereinafter abbreviated as DMT). Alternatively, various decomposed products may be molten and solidified in the recovery apparatus to damage the devices.

Examples of the chemical recycle may include: the method described in JP-A-11-21374, in which polyester wastes are hydrolyzed in the presence of an alkali compound to obtain terephthalic acid (which may be hereinafter abbreviated as TA), and the method described in U.S. Pat. No. 5,952,520 in which DMT and EG are obtained by vapor phase MeOH decomposition in MeOH.

However, all of these require the reaction conditions of high temperatures of 200° C. or more. For this reason, when different types of plastics which start to decompose from 190° C. as PVC are mixed, the temperature range of the operation of carrying out chemical recycle is unfavorably restricted.

Further, in JP-A-2000-169623, the following process is proposed: PET wastes are decomposed with EG, and the resulting bis-β-hydroxy ethyl terephthalate (which may be hereinafter abbreviated as BHET) is purified by a thin film evaporation apparatus; and then, BHET is melt polycondensed to obtain PET. Also in this case, there is a step of applying a heat history of 200° C. or more. Thus, when a different type of plastic which tends to undergo thermal decomposition such as PVC is mixed, it is not possible to obtain PET with favorable physical properties.

Namely, in the chemical recycle, the impurity content of such a degree as not to cause a problem is higher than with the material recycle. However, in the pretreatment step, foreign matters are required to be removed almost completely. Whereas, it is generally known that PET for bottles is obtained in the following manner: by using DMT or TA, and EG as starting materials, oligomers are obtained by the ester interchange reaction or the esterification reaction, followed by the polycondensation reaction. Unless the DMT or TA of the raw material is not the highly purified one sufficiently low in impurity content, the resulting PET cannot be used for PET bottles.

Due to the circumstances in which there are various such restrictions, there has been no method in which the effective components of used PET bottles are recovered to obtain PET for PET bottles again with the chemical recycle process.

Whereas, when polyester fibers are targeted for recovery, mixing of polyester fibers containing a dye may be unavoidable. The dye contained in the dyed polyester fibers undergoes thermal decomposition during a series of reactions such as depolymerization at high temperatures in the presence of a catalyst. The thermally decomposed products are dispersed in the recovered useful components, and remarkably degrade the quality of the recovered useful components. As an example of the method in which such problems are mentioned, and countermeasures are taken, mention may be made of the method described in JP-A-2004-217781. However, the number of methods disclosed heretofore is small. Further, the methods are not capable of achieving a sufficient recovery efficiency.

DISCLOSURE OF THE INVENTION

It is an object of the present invention to establish an efficient and economical useful component recovery method capable of solving the problems possessed by the related art, and obtaining recovered monomers usable for production of high purity polyester from dyed polyester fibers. Still other objects and advantages of the invention will be apparent from the following description.

BEST MODE FOR CARRYING OUT THE INVENTION

In accordance with one embodiment of the present invention, there is provided a method for recovering useful components from a dyed polyester fiber, which includes a dye extraction step, a solid liquid separation step, a depolymerization reaction step, an ester interchange reaction step, and a useful component separation step, the dye extraction step being a step of extracting and removing a dye at the glass transition temperature of the polyester or higher and at 220° C. or less by an extracting solvent including xylene and alkylene glycol from the dyed polyester fiber, the solid liquid separation step being a step of separating a dye-extracted polyester fiber and a dye-containing extracting solvent after the dye extraction step, the depolymerization reaction step being a step of allowing the dye-extracted polyester fiber to undergo a depolymerization reaction with alkylene glycol in the presence of a depolymerization catalyst, thereby to obtain a depolymerized solution containing bis-ω-hydroxy alkylene terephthalate (which may be hereinafter referred to as BHAT), the ester interchange reaction step being a step of allowing the depolymerized solution to undergo an ester interchange reaction by an ester interchange catalyst and methanol, and the useful component separation step being a step of separating and recovering dimethyl terephthalate and alkylene glycol from the ester interchange reaction product mixture obtained in the ester interchange reaction step. This is because this method enables the recovery of high purity useful components from a dyed polyester fiber with ease. Further, herein, the term "the useful components" represents the components useful to be recovered for manufacturing a polyester fiber, and represents the components mainly serving as the raw materials for polyester.

It is also preferable that the method includes at least one step selected from a group consisting of a solid matter removing step of removing solid matters during the process or after the process of the depolymerization reaction step, a depolymerized solution concentration step of distilling or evaporating a part of xylene and/or alkylene glycol from the depolymerized solution during the process or after the process of the depolymerization reaction step, and a polyamide dissolution and removal step of dissolving and removing polyamide.

As the object to be recovered, the polyester fiber is preferably a fiber including polyethylene terephthalate.

Below, embodiments of the invention will be described by way of Examples and the like. Incidentally, these Examples and descriptions illustrate the invention, and do not restrict the scope of the invention. It is needless to say that other embodiments may also fall within the scope of the invention so long as they are in agreement with the gist of the invention. For example, in the invention, "step" does not represent only the step recognizable distinguishably from others. The one combined with other operations, the one dispersed in a plurality of steps in actuality, the one including other step elements contained in this "step", or the one capable of carrying out the operations of a plurality of steps at one step may also fall within the scope of the invention so long as they are in agreement with the gist of the invention.

In the useful component recovery method of the invention, as the targeted polyester fibers, typically, fibers including polyethylene terephthalates and fibers including other polyalkylene terephthalates may be exemplified. Further, the fibers including polyalkylene terephthalates may contain therein other materials such as nylon and cotton in the form of blended fabric, and may contain other plastic components to be used for the purpose of surface modification or the like.

In the useful component recovery method of the invention, first, in the dye extraction step, a dye is extracted and removed from the dyed polyester fiber. In the dyed polyester fiber, various disperse dyes or the like are used. The fiber often contain the components which reduce the purity or the physical properties of the useful components to be recovered, such as a diazo group and halogen groups (Cl and Br) in the molecule of the disperse dye.

When the dyed polyester is subjected with these components contained therein to a depolymerization reaction by alkylene glycol in the presence of a catalyst, the cleavage reaction of the diazo group or elution of halogen atoms concurs. This remarkably reduces the purity and the physical properties of the useful components to be recovered.

On the other hand, the disperse dye and the like are bonded with the polyester fiber through an intermolecular force, so that the dye can be extracted and removed from the polyester fiber with solvent extraction. For example, there can be exemplified the method in which a dye or a surface finishing agent is removed from a polyester fiber by methylene chloride described in U.S. Pat. No. 3,806,316. However, when methylene chloride is mixed in the depolymerization reaction step, there is a high possibility that chlorine atoms contained in methylene chloride itself may be mixed in the recovered useful components. Therefore, methylene chloride is not suitable as an extracting solvent. Further, in order to avoid mixing of methylene chloride in the step, a drying step of removing methylene chloride is required to be provided. Drying requires enormous equipment and energy, and hence this method is very disadvantageous in terms of the cost.

As a result of various studies, we found out that these problems can be solved by using, as a dye extracting solvent, xylene and alkylene glycol in combination as an extracting solvent. Thus, we completed the invention. Herein, the xylene to be used as an extracting solvent is a solvent mainly including xylene. Whereas, the alkylene glycol to be used as an extracting solvent is a solvent mainly including alkylene glycol. Whereas, the use of xylene and alkylene glycol in combination as an extracting solvent includes at least one selected from a group consisting of the use of alkylene glycol and xylene in mixture, the use of alkylene glycol after use of xylene, and the use of xylene after use of alkylene glycol.

Use of xylene as a dye extracting solvent properly results in that xylene is left in the polyester fabric, which leads to the degradation of the quality of the useful components to be recovered. However, the boiling point of xylene is 138° C. to 144° C., and hence, at the time of dye extraction using alkylene glycol after extraction using xylene, or at the time of the depolymerization reaction using alkylene glycol, it is possible to remove most of xylene from the polyester fabric.

For the xylene to be used in the dye extraction step, at least one xylene selected from a group consisting of mixed xylene, paraxylene, metaxylene, and orthoxylene is preferably used. These may be used alone, or may be used in mixture of two or more thereof. Herein, the mixed xylene represents a mixture of paraxylene, metaxylene, orthoxylene, and ethylbenzene, and the composition ratio does not matter particularly.

Whereas, the amount of xylene for use in the dye extraction step is preferably 4 parts by weight to 12 parts by weight per 1 part by weight of the dyed polyester. When the amount of xylene to be used is less than 4 parts by weight per 1 part by weight of the dyed polyester, there is a possibility that the extraction of the dye cannot be carried out sufficiently. On the other hand, when the amount of xylene to be used is more than 12 parts by weight per 1 part by weight of the dyed polyester, the extraction of the dye can be carried out to a sufficient degree. However, an excessive energy becomes necessary for recovering pure xylene from the xylene in which the dye is dissolved or dispersed, which is not preferable. The wording "the amount of xylene" represents, supposing that batch type operations of carrying out a plurality of dye extraction operations are carried out, the total parts by weight of the xylene used in a plurality of the dye extraction operations per 1 part by weight of the dyed polyester to be subjected to the dye extraction operations. When a continuous type dye extraction operation is carried out, the wording represents the parts by weight of xylene which has contributed to the dye extraction operation per 1 part by weight of the dyed polyester completely subjected to the dye extraction operation.

In the invention, alkylene glycol for use in the dye extraction step is preferably alkylene glycol capable of forming the skeleton structure of the polyester fiber targeted for the useful component recovery. Namely, alkylene glycol for use in the dye extraction step is preferably alkylene glycol forming the repeating units of polyester forming the polyester fiber. More preferably, it is preferably alkylene glycol forming the main repeating unit of polyester. This is because the problem of mixing of the solvent, and the problem of disadvantage in cost due to the installation of drying equipment as described above can be avoided.

Whereas, it is preferable that alkylene glycol for use in the dye, extraction step and alkylene glycol for use in the depolymerization reaction step are the same type of alkylene glycol. This is because the following and other advantages are obtained: useful components with good quality become more likely to be obtained; the recovery of useful components, particularly, alkylene glycol, becomes easy; and recycling of alkylene glycol through the dye extraction step, the depolymerization reaction step, and the like becomes possible.

For example, the case where the alkylene glycol for use in the dye extraction step, the alkylene glycol forming the repeating unit of the polyester fiber targeted for the useful component recovery, and the alkylene glycol for use in the depolymerization reaction step are the same type of alkylene glycol is one preferred embodiment. This is for the following reason. Even when alkylene glycol is left in the dye-extracted polyester fiber after dye extraction, it is possible to recover high purity useful components without adversely affecting the step for the subsequent useful component recovery step at all. As a result, it is possible to simplify the steps, which is very advantageous economically.

As the examples of alkylene glycol for use in the dye extraction step, at least one glycol selected from a group consisting of ethylene glycol, diethylene glycol, 1,3-propanediol, and 1,4-butanediol is preferably used. These may be used alone, or may be used in mixture of two or more thereof.

Incidentally, as the alkylene glycol forming the repeating unit of the polyester fiber, for example, ethylene glycol can be exemplified when the polyester fiber includes polyethylene terephthalate; 1,3-propanediol, when the polyester fiber includes polytrimethylene terephthalate; and 1,4-butanediol, when the polyester fiber includes polybutylene terephthalate. For a polymer having the ethylene terephthalate structure and the butylene terephthalate structure, any of ethylene glycol, 1,4-butanediol, and a mixture of ethylene glycol and 1,4-butanediol is acceptable.

Whereas, it is preferable that the amount of alkylene glycol for use in the dye extraction step is 4 parts by weight to 10 parts by weight per 1 part by weight of the dyed polyester. When the amount of alkylene glycol to be used is less than 4 parts by weight per 1 part by weight of the dyed polyester, there is a possibility that the extraction of the dye cannot be carried out sufficiently. On the other hand, when the amount of alkylene glycol to be used is more than 10 parts by weight per 1 part by weight of the dyed polyester, the extraction of the dye can be carried out to a sufficient degree. However, an excessive energy becomes necessary for recovering pure alkylene glycol from the alkylene glycol in which the dye is dissolved or dispersed, which is not preferable. Further, alkylene glycol becomes another substance involving an undesirable side reaction. Accordingly, the recovery of alkylene glycol is reduced. This is also undesirable. Specifically, mention may be made of an example in which diethylene glycol is formed from ethylene glycol. The wording "the amount of alkylene glycol" represents, supposing that batch type operations of carrying out a plurality of dye extraction operations are carried out, the total parts by weight of the alkylene glycol used in a plurality of the dye extraction operations per 1 part by weight of the dyed polyester to be subjected to the dye extraction operations. When a continuous type dye extraction operation is carried out, the wording represents the parts by weight of alkylene glycol which has contributed to the dye extraction operation per 1 part by weight of the dyed polyester completely subjected to the dye extraction operation.

When the dye extraction temperature is too high, thermal decomposition of the dye is resultantly caused. Conversely, when the dye extraction temperature is too low, the rate at which the extracting solvent diffuses into the polyester fiber becomes insufficient, which is not efficient. The dye extraction temperature is required to be equal to, or more than the glass transition temperature of polyester forming the polyester fiber, and equal to, or less than 220° C., and more preferably 120° C. to 210° C. Whereas, herein, when the polyester is PET, the glass transition temperature is about 70° C. For example, in the case where dye extraction is desired to be carried out at 210° C. using paraxylene as xylene for use as an extracting solvent, and using ethylene glycol as alkylene glycol for use as an extracting solvent, the dye extraction can be carried out without a problem when the dye extraction operation is carried out under pressure. Further, in view of the efficiency of extraction, less likelihood to cause the degradation of quality of polyester, and the amount of the residual solvent being small in the depolymerization reaction step, preferably, in the dye extraction step, the temperature of extraction using alkylene glycol is 100 to 200° C., the temperature of extraction using xylene is 100 to 144° C. Further, the equipment for the dye extraction step may be simple equipment for execution. Therefore, in the dye extraction step, the pressure at the time of at least one dye extraction operation of those when alkylene glycol and xylene are used in mixture, when xylene is used, and when alkylene glycol is used is preferably atmospheric pressure.

As the system for dye extraction, any of a batch type reaction tank and a countercurrent continuous reaction tank may be adopted. In order to more reduce the amount of the extracting solvent to be used in total for obtaining the desirable discoloration degree (extraction degree), a countercurrent continuous reaction tank is preferably adopted. After the completion of dye extraction, the useful components may be recovered with any methods including known methods. Below, one example thereof will be shown.

After the completion of dye extraction, in the solid liquid separation step, the dye-containing extracting solvent and the dye-extracted polyester fiber can be separated from each other. Separation thereof can prevent the occurrence of a difficulty that stirring becomes impossible to perform due to the hindrance by solid matters, or other difficulties. Further, it can simultaneously reduce the amount of alkylene glycol to be used in the depolymerization reaction step. This is not only economically advantageous because this can shorten the depolymerization reaction time, but also this is useful because this can contribute to the improvement of the quality of the useful components to be finally recovered.

As the solid liquid separation method, a known solid liquid separation method such as pressure filtration by a pressure filter or a nitrogen gas, vacuum suction filtration, or centrifugation is applicable. Whereas, when a desirable discoloration degree cannot be obtained in the batch type operations, it is effective that the dye extraction operation is repeated again with alkylene glycol.

From the dye-containing extracting solvent after the completion of dye extraction, xylene and/or alkylene glycol can be recovered by distillation in the extracting solvent recovery step. Then, they can be used as xylene and alkylene glycol for use in the dye extraction step again, which is economically effective. Specifically, it is preferable that distillation is carried out after the solid liquid separation step. Heating is carried out under the conditions of the pressure, temperature, and the like, corresponding to the boiling point of xylene or alkylene glycol, which allows xylene and/or alkylene glycol to be recovered in a fractionating column or the like. Incidentally, at this step, distillation of the dye-containing extracting solvent and distillation of other alkylene glycol, or the like may be carried out together. This is because simplification in terms of equipment can be achieved when the distillation column is designed, further resulting in economical advantage.

In the depolymerization reaction step, the dye-extracted polyester fiber can be allowed to react with alkylene glycol in the presence of a depolymerization catalyst, resulting in a depolymerized solution containing bis-o-hydroxy alkylene terephthalate (BHAT). This solution may contain oligomers mixed therein. As previously described, as alkylene glycol for use in the depolymerization reaction, for example, the alkylene glycol obtained by recovery from the dye extraction step is preferably used.

More specifically describing the depolymerization reaction step, it is preferable that the depolymerization reaction is effected in an excess of alkylene glycol using a known depolymerization catalyst in a known catalyst concentration under a temperature of 120 to 210° C. When the temperature of the depolymerization reaction is less than 120° C., the depolymerization reaction time becomes very long, resulting in inefficiency. On the other hand, when the temperature of the depolymerization reaction exceeds 210° C., thermal decomposition of a lubricant or the like contained in the polyester fiber becomes noticeable. Then, a nitrogen compound, and the like formed from the thermal decomposition diffuse into the depolymerized solution, and they are difficult to separate at the post process of the useful component recovery. Therefore, it is not preferable that the temperature of the depolymerization reaction exceeds 210° C. Preferably, the temperature of the depolymerization reaction is 140 to 190° C. In this regard, with existing chemical recycle technologies, operations at high temperatures are required, and hence it has been difficult to take measures upon thermal decomposition of the lubricant.

It is useful to remove solid matters during the process or after the process of the depolymerization reaction step. This step is referred to as a solid matter removing step. In the solid matter removing step, it is possible to float and separate the fiber including different types of plastics such as polyethylene and polypropylene which could not be eliminated in the previous pretreatment process. The fiber including different types of plastics has a smaller specific gravity than that of alkylene glycol which is a solvent for the depolymerization reaction, and it floats onto the liquid surface of the depolymerized solution. Thus, this is subjected to phase separation as floatage agglomerates, and then extracted to be removed. This method is easy, and hence it is preferable.

In the solid matter removing step, different fibers such as cotton may, be filtrated and selected after the depolymerization reaction. These have a larger specific gravity than that of alkylene glycol, and are the components which cannot be separated as floatage agglomerates. Thus, in the solid matter removing step, it is possible to remove solid matters at large including the ones having a smaller specific gravity and the ones having a larger specific gravity than that of alkylene glycol. As the methods for removing solid matters at large, known methods other than those described above can also be adopted.

Incidentally, when polyamide such as nylon is mixed in the polyester fiber, this decomposes in the depolymerization reaction step. Thus, a nitrogen compound such as ε-caprolactam is mixed into the useful components to be recovered, and separation thereof becomes difficult. Under such circumstance, it is effective to incorporate a polyamide dissolution and removal step of dissolving and removing solidified matters containing polyamide such as nylon. Preferably, the step is incorporated prior to the depolymerization reaction step so as not to adversely affect the depolymerization reaction.

Specific methods for dissolving and removing polyamide may be any of known methods. However, for example, an object containing polyamide such as nylon to be recovered is charged in alkylene glycol, phenol, cresol, or a mixed solvent of phenol and ethylene chloride, and heating is carried out to 100 to 190° C. This enables dissolution and removal thereof. Incidentally, this step may be carried out at the same time in the dye extraction step.

At least a part of xylene and/or alkylene glycol can be distilled or evaporated from the solid matter-removed depolymerized solution, thereby to concentrate the depolymerized solution. This step is referred to as the depolymerized solution concentration step. By carrying out this step, it is possible to reduce the loads in terms of equipment and energy of the subsequent steps. Further, it is possible to achieve the effective use of the recovered alkylene glycol. The solid matters have been removed, and hence this concentration can be carried out with ease. However, the method of the invention shall not preclude its application to a depolymerized solution from which solid matters have not been removed.

In the depolymerized solution concentration step, alkyleneglycol is preferably distilled away until the alkylene glycol is in an amount of 0.5 to 2.0 parts by weight per 1 part by weight of the dyed polyester fiber charged as a raw material. The alkylene glycol distilled away at this step can be used for the dye extraction step or the depolymerization reaction step, again.

As for the depolymerized solution, the ester interchange reaction can be carried out by an ester interchange catalyst and methanol. This step is referred to as an ester interchange reaction step. This step can convert the useful components into dimethyl terephthalate and alkylene glycol. Incidentally, the depolymerized solution at this step may be any of a solid matter-unremoved depolymerized solution, a solid matter-removed depolymerized solution, or a depolymerized solution after concentration. However, it is preferably a solid matter-removed depolymerized solution or a depolymerized solution after concentration, and more preferably a depolymerized solution after concentration.

In the ester interchange reaction step, it is possible to effect the ester interchange reaction of BHAT in the depolymerized solution and methanol in the presence of an ester interchange catalyst with a known concentration. Thereafter, solid liquid separation is preferably carried out by a solid liquid separation means such as centrifugation. From the ester interchange reaction product mixture obtained in the ester interchange reaction step, dimethyl terephthalate and alkylene glycol can be separated and recovered. This step is referred to as a useful component separation step. Whereas, as the ester interchange catalyst, an already known alkali metal compound, alkaline-earth metal compound, manganese compound, or tin compound can be used.

Namely, in the useful component separation step, crude dimethyl terephthalate and crude alkylene glycol obtained in the ester interchange reaction step are purified by a purification method such as distillation, thereby to obtain high purity purified dimethyl terephthalate and purified alkylene glycol. At this step, foreign matters and impurities which have passed through the previous steps are captured at the distillation column bottom. Therefore, the recovered useful components do not contain these foreign matters and impurities, so that high purity ones can be obtained. When as the polyester fiber, a fiber including polyethylene terephthalate is used, purified dimethyl terephthalate and ethylene glycol can be obtained.

EXAMPLES

Below, the contents of the invention will be described more specifically by way of Examples. Incidentally, the respective numerical values in Examples were determined in the following manner.

(Nitrogen Content)

The content of nitrogen contained in a polyester fabric and the recovered useful components (ethylene glycol and dimethyl terephthalate) was determined by means of a trace total nitrogen analysis apparatus (TN-110 manufactured by Mitsubishi Chemical Corporation).

(Outward Appearance)

The recovered useful components were visually observed. Then, when coloration caused by a dye or coloration of yellow caused by thermal decomposition was not observed, the sample was judged as a good product. When the coloration of yellow was observed, the sample was judged as a defective product.

(Acid Value)

A sample was dissolved in an ethanol/paraxylene mixed solution, and titrated with potassium hydroxide by the use of an indicator. The number of milligrams of potassium hydroxide to be required for neutralizing the acid components contained in 1 g of the sample is referred to as the acid value. When the acid value was 10 mg/g or less, the sample was judged as a good product.

(Melt Colorimetry (Melt Hazen Color Number {APHA}))

According to the color number testing method shown in JIS K-4101, flat bottom Pyrex (registered trademark) calorimetric tube with a diameter of 23 mm and a wall thickness of 1.5 mm was used to measure the melt Hazen color number at a liquid depth of 140 mm in molten state by comparison with standard Hazen matching solutions. Whereas, for the melt apparatus, the aluminum ingot hot bath shown in JIS K-4101 was used, and that was used not only for melting, but also for holding the molten state. When the measured melt colorimetry was 50 or less, the sample was judged as a good product.

(Sulfuric Acid Ash Content)

The measurement was carried out according to ASTMD874.

(Diethylene Glycol Content)

The content of diethylene glycol in the ethylene glycol obtained by recovery was measured by means of a gas chromatograph (HP6850 model manufactured by Hewlett-Packard) When the measured diethylene glycol content was 0.5 wt % or less, the sample was judged as a good product.

(Moisture Content)

The moisture content in diethylene glycol in the ethylene glycol obtained by recovery was measured by means of a Karl Fischer moisture meter (MKC-210, manufactured by Kyoto Electronics Manufacturing Co., Ltd.). When the measured moisture content was 0.1 wt % or less, the sample was judged as a good product.

Example 1

100 g of cut pieces of polyethylene terephthalate fabric dyed in black (nitrogen content in fabric prior to dye extraction: 900 ppm) which was a dyed polyester fiber to be subjected to the method of the invention, and 600 g of paraxylene were charged into a 2 L separable flask. A dye extraction step was carried out by performing heating and stirring under atmospheric pressure at 130° C. for 10 minutes. After the completion of extraction, as a solid liquid separation step, suction filtration with an aspirator was carried out, thereby to separate dye-containing paraxylene from the fabric from which the dye had been extracted (dye-extracted polyester fiber).

Thereafter, the dye-extracted polyester fiber and 600 g of another paraxylene were charged into a separable flask, and extraction of the dye was carried out under the same conditions. After the completion of extraction, solid liquid separation was carried out again, thereby to separate dye-containing paraxylene and the fabric from which the dye had been extracted and removed.

Subsequently, about 100 g of the fabric from which the dye had been extracted and removed and 600 g of another ethylene glycol were charged into a separable flask. A dye extraction step was carried out by performing heating and stirring under atmospheric pressure at 170° C. for 10 minutes. Most of the paraxylene contained in the fabric is evaporated through an exhaust tube by heating at this step. The evaporated paraxylene is recovered by a condenser. After the completion of extraction, a solid liquid separation step was carried out again, thereby to separate a dye-containing ethylene glycol from the fabric from which the dye had been extracted and removed.

Subsequently, as a depolymerization reaction step, 100 g of the dye-extracted fabric was charged into a mixture of 400 g of ethylene glycol preheated up to 185° C., and 3 g of potassium carbonate as a depolymerization catalyst. That was allowed to react under atmospheric pressure at 185° C. for 4 hours, thereby to obtain a depolymerized solution containing bis-β-hydroxy ethylene terephthalate (BHET).

Incidentally, after the depolymerization reaction at the depolymerization reaction step, solid matters were filtrated and removed by a wire gauze strainer with an opening of 350 μm$^3$. In this solid matter removing step, it was possible to mainly remove different types of plastics other than polyester.

The resulting depolymerized solution after filtration was fed to a distillation column, and a depolymerized solution concentration step of distilling away 300 g of ethylene glycol under the conditions of a column bottom temperature of 140 to 150° C. and a pressure of 13.3 kPa, and thereby concentrating the depolymerized solution was carried out. Then, to 200 g of the filtrated and concentrated depolymerized solution, 1.7 g of potassium carbonate as an ester interchange catalyst, and 200 g of methanol were added. Thus, an ester interchange reaction step was carried out under atmospheric pressure at 75 to 80° C. for 1 hour, thereby to obtain an ester interchange reaction product mixture.

After the completion of the ester interchange reaction, the ester interchange reaction product mixture was cooled to 40° C. Then, a solid liquid separation step of achieving solid liquid separation between a cake containing crude dimethyl terephthalate as a main component and a filtrate containing methanol and crude ethylene glycol as main components was carried out by centrifugation.

Then, crude dimethyl terephthalate was subjected to distillation under the conditions of a pressure of 6.7 kPa and a column bottom temperature of 180 to 200° C., thereby to obtain purified dimethyl terephthalate (step of separating useful components of DMT components). Further, similarly, crude ethylene glycol was subjected to distillation under the conditions of a pressure of 13.3 kPa and a column bottom temperature of 140 to 150° C., thereby to obtain purified ethylene glycol (step of separating useful components of EG components) Finally, as useful components, purified dimethyl terephthalate and purified ethylene glycol were obtained in a yield of 85 wt %, respectively.

Purified dimethyl terephthalate recovered from the ester interchange reaction product mixture bore comparison with commercially available products in terms of the inspection items such as outward appearance, acid value, melt colorimetry, and sulfuric acid ash content. Whereas, the purified ethylene glycol recovered from the ester interchange reaction product mixture bore comparison with commercially available products in terms of the inspection items such as diethylene glycol content and moisture content. Further, any nitrogen content of the recovered purified dimethyl terephthalate and the recovered purified ethylene glycol was equal to, or lower than the lower detection limit. Thus, high purity useful components were obtained.

Whereas, 1200 g of the dye-containing paraxylene obtained in the dye extraction step was distilled under the conditions of a column bottom temperature of 120 to 130° C. and a pressure of 40.0 kPa, so that 1100 g thereof was obtained as a distilled component. For such paraxylene obtained in the extracting solvent recovery step, the coloration due to mixing of a dye was not observed in outward appearance, and the nitrogen content was also equal to, or lower than the lower detection limit. As a result of these operations, it was possible to recover paraxylene in such a purity as to allow reuse thereof as an extracting solvent.

Whereas, 600 g of the dye-containing ethylene glycol obtained in the dye extraction step was distilled under the conditions of a column bottom temperature of 140 to 150° C. and a pressure of 13.3 kPa, so that 536 g thereof was obtained as a distilled component. For such ethylene glycol obtained in the extracting solvent recovery step, the coloration due to mixing of a dye was not observed in outward appearance, and the nitrogen content was also equal to, or lower than the lower detection limit. As a result of these operations, it was possible to recover ethylene glycol in such a purity as to allow reuse thereof as an extracting solvent or a raw material for polyethylene terephthalate.

Example 2

100 g of cut pieces of polyethylene terephthalate fabric dyed in black (nitrogen content in fabric prior to dye extraction: 900 ppm) which was a dyed polyester fiber to be subjected to the method of the invention, and 600 g of ethylene glycol were charged into a 2 L separable flask. A dye extraction step was carried out by performing heating and stirring under atmospheric pressure at 170° C. for 10 minutes. After the completion of extraction, as a solid liquid separation step, suction filtration with an aspirator was carried out, thereby to separate a dye-containing ethylene glycol from the fabric from which the dye had been extracted (dye-extracted polyester fiber).

Thereafter, the dye-extracted polyester fiber and 600 g of another paraxylene were charged into a separable flask, and for extraction of the dye, a step of extracting the dye was carried out by performing heating and stirring under atmospheric pressure at 130° C. for 10 minutes. After the completion of extraction, solid liquid separation was carried out again, thereby to separate a dye-containing paraxylene and the fabric from which the dye had been extracted and removed.

Subsequently, about 100 g of the fabric from which the dye had been extracted and removed and 600 g of another paraxylene were charged into a separable flask. Then, extraction of the dye was carried out under the same conditions. After the completion of extraction, solid liquid separation was carried out again, thereby to separate a dye-containing paraxylene from the fabric from which the dye had been extracted and removed.

Subsequently, as a depolymerization reaction step, 100 g of the dye-extracted fabric was charged into a mixture of 400 g of ethylene glycol preheated up to 185° C., and 3 g of potassium carbonate as a depolymerization catalyst. That was allowed to react under atmospheric pressure at 185° C. for 4 hours, thereby to obtain a depolymerized solution containing bis-β-hydroxy ethylene terephthalate (BHET). Thereafter, in the same manner as in Example 1, through the solid matter removing step, the depolymerized solution concentration step, the ester interchange reaction step, the solid liquid separation step, and step of separating useful components of DMT components, finally, dimethyl terephthalate was obtained in a yield of 87 wt %, and ethylene glycol was obtained in a yield of 84 wt % as useful components.

The dimethyl terephthalate recovered from the ester interchange reaction product mixture bore comparison with commercially available products in terms of the inspection items such as outward appearance, acid value, melt colorimetry, and sulfuric acid ash content. Whereas, the ethylene glycol recovered from the ester interchange reaction product mixture bore comparison with commercially available products in terms of the inspection items such as diethylene glycol content and moisture content. Further, any nitrogen content of the recovered dimethyl terephthalate and the recovered ethylene glycol was equal to, or lower than the lower detection limit. Thus, high purity useful components were obtained.

Whereas, 1200 g of the dye-containing paraxylene obtained in the dye extraction step was distilled under the conditions of a column bottom temperature of 120 to 130° C. and a pressure of 40.0 kPa, so that 1089 g thereof was obtained as a distilled component. For such paraxylene obtained in the extracting solvent recovery step, the coloration due to mixing of a dye was not observed in outward appearance, and the nitrogen content was also equal to, or lower than the lower detection limit. As a result of these operations, it was possible to recover paraxylene in such a purity as to allow reuse thereof as an extracting solvent.

Whereas, 600 g of the dye-containing ethylene glycol obtained in the dye extraction step was distilled under the conditions of a column bottom temperature of 140 to 150° C. and a pressure of 13.3 kPa, so that 540 g thereof was obtained as a distilled component. For such ethylene glycol obtained in the extracting solvent recovery step, the coloration due to mixing of a dye was not observed in outward appearance, and the nitrogen content was also equal to, or lower than the lower detection limit. As a result of these operations, it was possible to recover ethylene glycol in such a purity as to allow reuse thereof as an extracting solvent or a raw material for polyethylene terephthalate.

Example 3

100 g of cut pieces of polyethylene terephthalate fabric dyed in black (nitrogen content in fabric prior to dye extraction: 900 ppm) which was a dyed polyester fiber to be subjected to the method of the invention, 600 g of paraxylene, and 300 g of ethylene glycol were charged at the same time into a 2 L separable flask. A dye extraction step was carried out by performing heating and stirring under atmospheric pressure at 135° C. for 10 minutes. After the completion of extraction, as a solid liquid separation step, suction filtration with an aspirator was carried out, thereby to separate a dye-containing ethylene glycol, paraxylene mixed solvent from the fabric from which the dye had been extracted (dye-extracted polyester fiber).

Thereafter, the dye-extracted polyester fiber, 600 g of another paraxylene, and 300 g of another ethylene glycol were charged into a separable flask, and a step of extracting the dye was carried out by performing heating and stirring under atmospheric pressure at 135° C. for 10 minutes. After the completion of extraction, solid liquid separation was carried out, thereby to separate a dye-containing paraxylene, ethylene glycol mixed solution and the fabric from which the dye had been extracted and removed.

Subsequently, as a depolymerization reaction step, 100 g of the dye-extracted fabric was charged into a mixture of 400 g of ethylene glycol preheated up to 185° C., and 3 g of potassium carbonate as a depolymerization catalyst. That was allowed to react under atmospheric pressure at 185° C. for 4 hours, thereby to obtain a depolymerized solution containing bis-β-hydroxy ethylene terephthalate (BHET). Thereafter, in the same manner as in Example 1, through the solid matter removing step, the depolymerized solution concentration step, the ester interchange reaction step, the solid liquid separation step, and the DMT distillation step, finally, dimethyl terephthalate was obtained in a yield of 83 wt %, and ethylene glycol was obtained in a yield of 82 wt % as useful components.

The dimethyl terephthalate recovered from the ester interchange reaction product mixture bore comparison with commercially available products in terms of the inspection items such as outward appearance, acid value, melt colorimetry, and sulfuric acid ash content. Whereas, the ethylene glycol recovered from the ester interchange reaction product mixture bore comparison with commercially available products in terms of the inspection items such as diethylene glycol content and moisture content. Further, any nitrogen content of the recovered dimethyl-terephthalate and the recovered ethylene glycol was equal to, or lower than the lower detection limit. Thus, high purity useful components were obtained.

Whereas, a mixture of about 1200 g of the paraxylene and about 600 g of ethylene glycol containing a dye obtained in the dye extraction step was allowed to stand still under ordinary temperatures, and was allowed to undergo phase separation into two layers. The paraxylene phase was distilled under the conditions of a column bottom temperature of 120 to 130° C. and a pressure of 40.0 kPa, so that 1087 g thereof was obtained as a distilled component. For such paraxylene obtained in the extracting solvent recovery step, the coloration due to mixing of a dye was not observed in outward appearance, and the nitrogen content was also equal to, or lower than the lower detection limit. As a result of these operations, it was possible to recover paraxylene in such a purity as to allow reuse thereof as an extracting solvent. Whereas, the ethylene glycol phase was distilled under the conditions of a column bottom temperature of 140 to 150° C. and a pressure of 13.3 kPa, so that 527 g thereof was obtained as a distilled component. For such ethylene glycol obtained in the extracting solvent recovery step, the coloration due to mixing of a dye was not observed in outward appearance, and the nitrogen content was also equal to, or lower than the lower detection limit. As a result of these operations, it was possible to recover ethylene glycol in such a purity as to allow reuse thereof as an extracting solvent or a raw material for polyethylene terephthalate.

Comparative Example 1

100 g of a polyethylene terephthalate fabric dyed in the same black as that used in Examples 1 to 3 was cut. Then, dimethyl terephthalate and ethylene glycol were recovered under the same conditions as in Example 1, except that the process did not go through the dye extraction step, and the solid liquid separation step. The dimethyl terephthalate recovered from the ester interchange reaction product mixture bore comparison with commercially available products in terms of the inspection items such as outward appearance, acid value, melt colorimetry, and sulfuric acid ash content. However, it contained 11 ppm by weight of nitrogen. Whereas, the ethylene glycol recovered from the ester interchange reaction product mixture bore comparison with commercially available products in terms of the inspection items such as diethylene glycol content and moisture content. However, it contained 45 ppm by weight of nitrogen. Thus, the degradation of the quality was observed.

Comparative Example 2

100 g of cut pieces of a polyethylene terephthalate fabric dyed in the same black as that used in Examples 1 to 3 and 1000 g of ethylene glycol were charged in a 5 L autoclave. Then, dimethyl terephthalate and ethylene glycol were recovered under the same conditions as in Examples 1 to 3, except that extraction of the dye was carried out by performing heating and stirring under a pressure of 430 kPa (absolute pressure) at a temperature of 240° C. for 30 minutes. The dimethyl terephthalate recovered from the ester interchange reaction product mixture bore comparison with commercially available products in terms of the inspection items such as outward appearance, acid value, melt colorimetry, and sulfuric acid ash content. The nitrogen content thereof was also equal to, or less than the lower detection limit. Thus, it was possible to obtain high purity useful components. Whereas, the ethylene glycol recovered from the ester interchange reaction product mixture bore comparison with commercially available products in terms of the inspection items such as diethylene glycol content and moisture content. However, it contained 15 ppm by weight of nitrogen. Thus, the degradation of the quality was observed.

INDUSTRIAL AVAILABILITY

The present invention provides a method for recovering high purity useful components from a dyed polyester fiber. Further, by using xylene and alkylene glycol in combination as a dye extracting solvent, it is possible to implement a more efficient and economical useful component recovery method as compared with conventional methods. Thus, the industrial significance is very large.

The invention claimed is:

1. A method for recovering useful components from a dyed polyester fiber, comprising a dye extraction step, a solid liquid separation step, a depolymerization reaction step, an ester interchange reaction step, and a useful component separation step, the dye extraction step being a step of extracting and removing a dye at the glass transition temperature of the polyester or higher and at 220° C. or less by an extracting solvent including xylene and alkylene glycol from the dyed polyester fiber, the solid liquid separation step being a step of separating a dye-extracted polyester fiber and a dye-containing extracting solvent after the dye extraction step, the depolymerization reaction step being a step of allowing the dye-extracted polyester fiber to undergo a depolymerization reaction with alkylene glycol in the presence of a depolymerization catalyst, thereby to obtain a depolymerized solution containing bis-ω-hydroxy alkylene terephthalate, the ester interchange reaction step being a step of allowing the depolymerized solution to undergo an ester interchange reaction by an ester interchange catalyst and methanol, and the useful component separation step being a step of separating and recovering dimethyl terephthalate and alkylene glycol from the ester interchange reaction product mixture obtained in the ester interchange reaction step.

2. The method for recovering useful components according to claim 1, comprising at least one step selected from a group consisting of a solid matter removing step of removing solid matters during the process or after the process of the depolymerization reaction step, a depolymerized solution concentration step of distilling or evaporating a part of xylene and/or alkylene glycol from the depolymerized solution during the process or after the process of the depolymerization reaction step, and a polyamide dissolution and removal step of dissolving and removing polyamide.

3. The method for recovering useful components according to claim 1, comprising an extracting solvent recovery step of recovering xylene and/or alkylene glycol from the dye-containing extracting solvent by distillation.

4. The method for recovering useful components according to claim 1, wherein the polyester fiber is a polyester fiber formed of polyester formed from a repeating unit formed from an alkylene glycol as a raw material, and the alkylene glycol in the dye extraction step is the same compound as the alkylene glycol which is a raw material for forming the repeating unit of the polyester forming the polyester fiber.

5. The method for recovering useful components according to claim 1, wherein the alkylene glycol in the dye extraction step is the same compound as the alkylene glycol in the depolymerization reaction step.

6. The method for recovering useful components according to claim 1, wherein xylene for use in the dye extraction step is at least one xylene selected from a group consisting of mixed xylene, paraxylene, metaxylene, and orthoxylene, and alkylene glycol for use in the dye extraction step is at least one alkylene glycol selected from a group consisting of ethylene glycol, diethylene glycol, 1,3-propanediol, and 1,4-butanediol.

7. The method for recovering useful components according to claim 1, wherein the dye extraction step is carried out in a batch type reaction tank or a countercurrent continuous reaction tank.

8. The method for recovering useful components according to claim 1, wherein the polyester fiber is a fiber including polyethylene terephthalate.

9. The method for recovering useful components according to claim 1, comprising at least one method selected from a group consisting of a method using alkylene glycol and xylene in mixture, a method using alkylene glycol after using xylene, and a method using xylene after using alkylene glycol, in the dye extraction step.

10. The method for recovering useful components according to claim 1, wherein in the dye extraction step, the extraction temperature for using alkylene glycol is the glass transition temperature of the polyester to 200° C., the extraction temperature for using xylene is the glass transition temperature of the polyester to 144° C., and the pressure in the dye extraction step is atmospheric pressure when the dye extraction step comprises one or more steps selected from the group consisting of applying alkylene glycol and xylene in a mixture, applying xylene, and applying alkylene glycol.

11. The method for recovering useful components according to claim 1, wherein the amount of alkylene glycol for use in the dye extraction step is 4 parts by weight to 10 parts by weight per 1 part by weight of the dyed polyester.

12. The method for recovering useful components according to claim 1, wherein the amount of xylene for use in the dye extraction step is 4 parts by weight to 12 parts by weight per 1 part by weight of the dyed polyester.

* * * * *